(12) United States Patent
Sato et al.

(10) Patent No.: US 7,851,047 B2
(45) Date of Patent: Dec. 14, 2010

(54) COMPOSITE SHEET AND PROCESS AND APPARATUS FOR PRODUCING THE SAME

(75) Inventors: Kenichi Sato, Tochigi (JP); Yoshinobu Machida, Tochigi (JP); Minoru Tsukada, Tochigi (JP); Yuichi Ishino, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/292,373

(22) Filed: Nov. 18, 2008

(65) Prior Publication Data
US 2009/0092797 A1    Apr. 9, 2009

Related U.S. Application Data

(62) Division of application No. 10/704,908, filed on Nov. 12, 2003, now Pat. No. 7,468,114.

(30) Foreign Application Priority Data

| Nov. 13, 2002 | (JP) | ............................. 2002-329213 |
| Oct. 10, 2003 | (JP) | ............................. 2003-351594 |
| Oct. 10, 2003 | (JP) | ............................. 2003-351691 |

(51) Int. Cl.
*B32B 3/00* (2006.01)
*B32B 3/12* (2006.01)
*A61F 13/15* (2006.01)

(52) U.S. Cl. .................. 428/166; 428/172; 428/178; 428/180; 604/385.01

(58) Field of Classification Search ................ 428/166, 428/172, 174, 178, 180; 604/358, 385.01
See application file for complete search history.

(56) References Cited

U.S. PATENT DOCUMENTS

| 2,115,577 A | 4/1938 | Goldman |
| 2,974,716 A | 3/1961 | Albert |
| 3,193,434 A * | 7/1965 | Weis ............................ 428/46 |
| 4,323,068 A | 4/1982 | Aziz |

(Continued)

FOREIGN PATENT DOCUMENTS

CN    1349789 A    5/2002

(Continued)

OTHER PUBLICATIONS

On-line translation of Matumura et al., JP 11-286863, published Oct. 19, 1999.

(Continued)

*Primary Examiner*—Donald Loney
(74) *Attorney, Agent, or Firm*—Birch, Stewart, Kolasch & Birch, LLP

(57) ABSTRACT

A composite sheet comprising an upper layer 2 and a lower layer 3 both made of a substantially inextensible sheet which are partially bonded to each other at a large number of joints 4. The upper layer 2 forms a large number of outward hollow projections 5 in the area other than the joints 4. The projections 5 and the joints 4 are arranged such that the projections and the joints alternate in one direction to make lines and that the projections in each of the lines are out of alignment with the projections in the adjacent lines.

4 Claims, 3 Drawing Sheets

U.S. PATENT DOCUMENTS

| | | | |
|---|---|---|---|
| 4,614,632 | A | 9/1986 | Kezuka et al. |
| 4,735,738 | A | 4/1988 | Willman |
| 5,558,923 | A | 9/1996 | Vesamaa et al. |
| 5,705,249 | A | 1/1998 | Takai et al. |
| 6,013,063 | A | 1/2000 | Roe et al. |
| 6,153,037 | A | 11/2000 | Kim et al. |
| 6,311,754 | B1 | 11/2001 | Marschke |
| 6,409,857 | B2 | 6/2002 | Pallas et al. |
| 2004/0140047 | A1 | 7/2004 | Sato et al. |

FOREIGN PATENT DOCUMENTS

| | | |
|---|---|---|
| EP | 0341993 A1 | 11/1989 |
| EP | 1184016 A | 3/2002 |
| EP | 1190690 A | 3/2002 |
| EP | 1226801 A | 7/2002 |
| JP | 35-16985 | 7/1960 |
| JP | 49-46062 | 4/1974 |
| JP | 2-18036 A | 1/1990 |
| JP | 3-111198 A | 5/1991 |
| JP | 5-59655 A | 3/1993 |
| JP | 6-304203 A | 11/1994 |
| JP | 10-245757 A | 9/1998 |
| JP | 11-504685 A | 4/1999 |
| JP | 11-286863 A | 10/1999 |
| JP | 2000-197930 A | 7/2000 |
| JP | 2002-165830 A | 6/2002 |
| JP | 2002-527642 A | 8/2002 |
| JP | 2003-33966 A | 2/2003 |
| JP | 2003-94125 A | 4/2003 |
| JP | 2003-521947 A | 7/2003 |
| JP | 2003-521969 A | 7/2003 |
| JP | 2004-174234 A | 6/2004 |
| JP | 2005-111908 A | 4/2005 |
| JP | 2005-319730 A | 11/2005 |
| JP | 2007-130817 A | 5/2007 |
| WO | 99/42068 A1 | 8/1999 |
| WO | 00/23024 A1 | 4/2000 |
| WO | WO 01/06974 A1 | 2/2001 |

OTHER PUBLICATIONS

Extended European Search Report issued in the corresponding European application No. 06012863.4 dated Jul. 22, 2009.
International Search Report dated Dec. 22, 2008 for International Application No. PCT/JP2008/069738.
JP 2007-276679; Notice of Rejection; Jun. 8, 2010; pp. 1-3.

* cited by examiner

COMPOSITE SHEET AND PROCESS AND APPARATUS FOR PRODUCING THE SAME

This Application is a Divisional of application Ser. No. 10/704,908, filed on Nov. 12, 2003, now U.S. Pat. No. 7,468,114 which claims priority on Japanese Patent Application Nos. 2002-329213 filed Nov. 13, 2002, 2003-351594 filed Oct. 10, 2003 and 2003-351691 filed Oct. 10, 2003. The entire contents of each of these applications are hereby incorporated by reference.

BACKGROUND OF THE INVENTION

The present invention relates to a composite sheet comprising two plies one of which has a large number of projections, and a process and an apparatus for producing the composite sheet. The composite sheet of the present invention is suited for use as an element, especially a topsheet, of absorbent articles such as sanitary napkins and disposable diapers.

JP-A-5-59655 discloses a bulky composite nonwoven fabric which is produced by adhering a spun-bond nonwoven fabric to at least one side of an elastic sheet material by point bonding to prepare a composite nonwoven fabric, stretching the composite nonwoven fabric in a prescribed direction, and releasing the stretching load to make the spun-bond nonwoven fabric wavy. This composite nonwoven fabric is used as a side belt of a pull-on diaper. Other known methods for obtaining composite sheets with a large number of projections include those disclosed in JP-A-10-245757 and JP-A-2-18036.

According to JP-A-5-59655, plastic deformation of the spun-bond nonwoven fabric is taken advantage of to make itself wavy, so that the wavy part of the composite sheet is fuzzy. When such a fuzzy sheet is used as a topsheet of an absorbent article, the fuzz would irritate the wearer's skin to reduce wearing comfort. Seeing that the composite nonwoven fabric is not contemplated for use as a topsheet of an absorbent article, its application as a topsheet of an absorbent article is not expected to prevent leakage of urine, still less a highly viscous liquid such as soft stool or menstrual blood.

Moreover, since the waviness results from plastic deformation of the spun-bond nonwoven fabric, it is difficult to always make protrusions of a given size with good reproducibility.

SUMMARY OF THE INVENTION

An object of the present invention is to provide a composite sheet free from the drawbacks of the above-described related arts, particularly a composite sheet suitable as a topsheet of an absorbent article, and a process and an apparatus for producing the composite sheet.

To accomplish the above object, the present invention provides a composite sheet comprising an upper layer made of a substantially inextensible sheet and a lower layer made of a substantially inextensible sheet which are partially bonded to each other at a large number of joints, the upper layer projecting outward to form a large number of hollow projections in the area other than the joints, and the projections and the joints being arranged such that the projections and the joints alternate in one direction to make lines and that the projections in each of the lines are out of alignment with the projections in the adjacent lines.

The present invention also provides a process of producing the above-described composite sheet which comprises embossing the sheet forming the upper layer through the mesh of a first roll having projections and depressions on the peripheral surface thereof and a second roll having projections and depressions mating with the depressions and the projections of the first roll on the peripheral surface thereof to make the upper layer and joining the embossed upper layer, while being vacuum held to the peripheral surface of the first roll, with the lower layer at the parts corresponding to the tops of the projections of the first roll.

The present invention also provides an apparatus for producing a composite sheet comprising a first and a second sheet which are partially bonded to each other at a large number of joints, the first sheet projecting in the area other than the joints to form a large number of hollow projections, the apparatus having a first roll having projections and depressions on the peripheral surface thereof and a second roll having projections and depressions mating with the depressions and the projections of the first roll on the peripheral surface thereof, wherein at least the first roll is composed of a plurality of gears mounted on a rotating axis to provide projections and depressions alternating in the rotating direction of the first roll, recesses having a prescribed width are provided for every given number of the gears, and each of the recesses connects to a suction path formed in the first roll and extending in the axial direction of the first roll.

BRIEF DESCRIPTION OF THE DRAWINGS

The present invention will be more particularly described with reference to the accompanying drawings, in which.

DETAILED DESCRIPTION OF THE PREFERRED EMBODIMENTS

Figure 1:
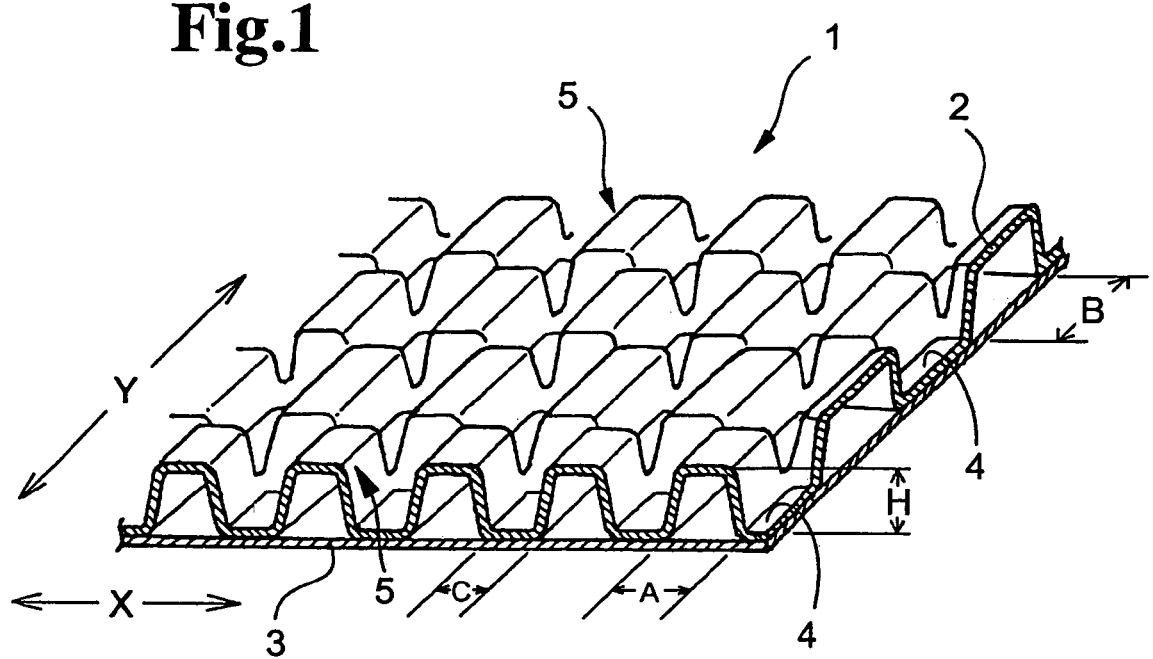
FIG. 1 is a perspective of a composite sheet according to the present invention.

The present invention will be described based on its preferred embodiments while referring to the accompanying drawings. FIG. 1 is a perspective of an example of the composite sheet according to the present invention. The composite sheet according to this embodiment is suited for use as an element of an absorbent article, such as a sanitary napkin or a disposable diaper, especially as a topsheet 1 that is disposed on the side to be brought into contact with a wearer's skin. The topsheet 1 shown in FIG. 1 has two plies, a first ply as an upper layer 2 disposed on the wearer's side and a second ply as a lower layer 3 disposed on the absorbent member's side. The upper layer 2 and the lower layer 3 are typically made of nonwoven fabric or film of various kinds.

The upper layer 2 and the lower layer 3 are partially bonded at a great number of joints 4. The upper layer 2 projects toward the wear's side in the area other than the joints 4 to form hollow projections 5.

In the embodiment shown in FIG. 1, each projection 5 is a flat rectangular prism or a flat truncated quadrangular pyramid with a rectangular base and rounded edges, and each joint 4 has a rectangular shape.

The projections 5 and the joints 4 are arranged alternately to make a line in a direction. In the embodiment shown in FIG.

1, the projections 5 and the joints 4 alternate in a line along direction X which agrees with the machine direction in the production of the topsheet 1. In application to an absorbent article, the direction X (i.e., MD) of the topsheet 1 agrees with either the longitudinal direction of the absorbent article or the direction perpendicular to the longitudinal direction. There are a large number of such lines of the alternating projections 5 and joints 4 arrayed in direction Y.

The projections in any of the lines and those in adjacent lines are out of alignment with each other. The expression "out of alignment" as used herein means that any projection in a line and a closest projection in an adjacent line are "not completely" side by side. Such an arrangement can be otherwise described as follows. Taking for instance an arbitrary projection in a line, there is no projection present in an adjacent line at the area exactly adjoining that projection. Therefore, every projection in X direction adjoins in Y direction a whole joint or a combination of a part of a joint and a part of a projection of an adjacent line. If projections of lines are aligned to form rows in Y direction, liquid would flow easily along these rows of projections to cause leakage.

In the embodiment shown in FIG. 1, the position of a joint in a line and the position of a closest joint of an adjacent line in X direction are different by a half of the pitch of the joints. Accordingly, every joint is a closed depressed area surrounded on all four sides by projections. In other words, the joints are arranged in a checkered pattern and so are the projections.

The projections 5 and the joints 4 being so disposed, an absorbent article having the topsheet 1 prevents leakage extremely effectively. For example, the topsheet 1 applied to disposable diapers, particularly those designed for a few months old babies having loose stool (highly viscous liquid), produces the following effects. In general, loose stool, being highly viscous, hardly passes through a topsheet but tends to stay and flow laterally on the topsheet. The topsheet 1 of the present embodiment traps loose stool in the closed depressions (joints 4) surrounded by the projections 5 and therefore hardly allows it to flow laterally. Being so trapped, loose stool is then pressed to migrate downward into the absorbent member. Leakage of loose stool is thus prevented. Besides, the projections 5, being hollow, produce an effect of hiding the color of soft stool absorbed by the absorbent member. The same effects are enjoyed when the topsheet 1 of the present embodiment is applied to sanitary napkins for absorbing menstrual blood, which is also a highly viscous liquid.

In order to enhance these effects, it is preferred for the projections 5 to have a height H (see FIG. 1) of from 1 to 10 mm, particularly 3 to 6 mm, a base dimension A of 2 to 30 mm, particularly 2 to 5 mm, in X direction, a base dimension B of 2 to 30 mm, particularly 2 to 5 mm in Y direction, and a base area of 4 to 900 mm$^2$, particularly 4 to 25 mm$^2$.

In order to prevent lateral flow of highly viscous liquid while providing a good feel to the touch and high cushioning properties, the joints 4 preferably have a length C (see FIG. 1) of 0.1 to 20 mm, particularly 0.5 to 5 mm, in X direction.

The upper layer 2 and the lower layer 3 are made of sheets of the same or different fibrous materials. These two sheets are substantially inextensible. By the use of such sheets, the topsheet 1 having an embossed pattern in substantial agreement with the mating projections and depressions formed on the first and second embossing rolls (hereinafter described) can be obtained in a stable manner and with satisfactory reproducibility. The expression "substantially inextensible" as used herein is intended to mean that the sheets have an elongation limit of 105% or lower and undergo destruction or permanent deformation at an elongation exceeding that limit.

Any sheet can be used to form the upper and lower layers as long as it is made of those materials that have been employed to make topsheets of conventional absorbent articles and is substantially inextensible. Useful sheets include nonwoven fabric prepared by carding, spun bonded nonwoven fabric, melt blown nonwoven fabric, spun laced nonwoven fabric, and needle punched nonwoven fabric. Films that are perforated and thereby made liquid-permeable are also usable. Constituent fibers of nonwoven fabrics used as the sheets preferably have a fineness of 1 to 20 dtex, particularly 1.5 to 4 dtex, for securing sufficient strength and satisfactory feel required of a topsheet. It is desirable that the two sheets be previously subjected to a hydrophilization treatment with a surface active agent, etc.

The basis weight of the upper layer 2 is preferably 10 to 100 g/m$^2$, still preferably 10 to 30 g/m$^2$, and that of the lower layer 3 is preferably 5 to 50 g/m$^2$, particularly 10 to 30 g/m$^2$. The basis weight of the topsheet 1 including the upper and the lower layers preferably ranges from 15 to 150 g/m$^2$, particularly 20 to 60 g/m$^2$.

Figure 2:
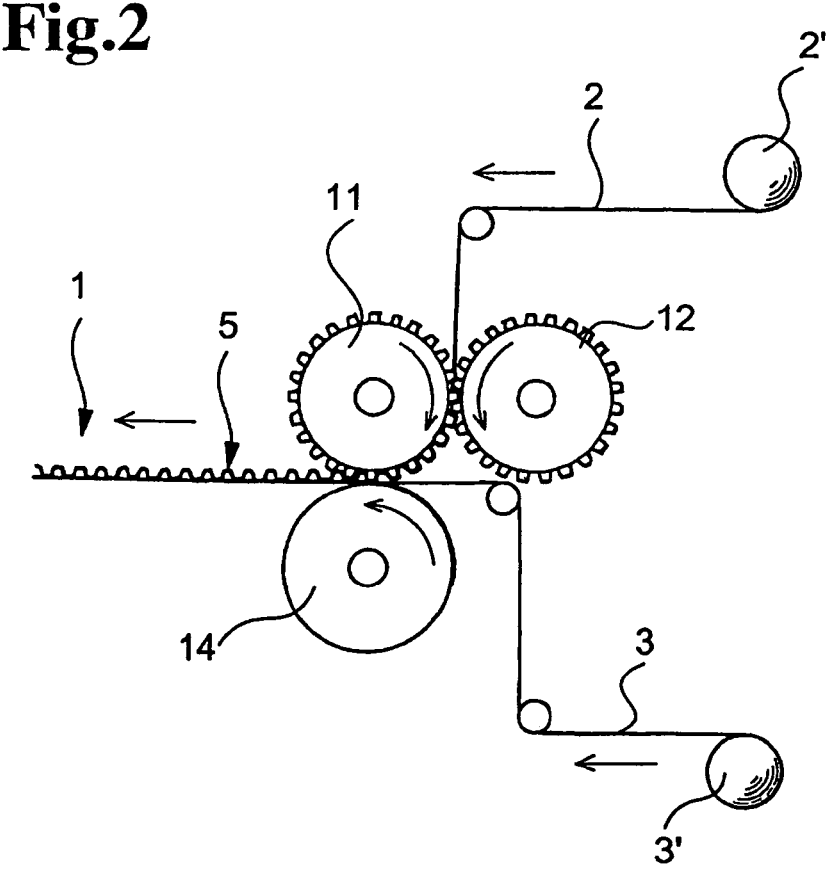
FIG. 2 schematically illustrates a process of producing the composite sheet shown in FIG. 1.

A process of producing the topsheet 1 according to the above-mentioned embodiment will then be described by referring to FIGS. 2 through 5. FIG. 2 shows an apparatus for producing the topsheet 1. The apparatus has a first roll 11 having projections on its surface, a second roll 12 having on its surface projections mating with those on the first roll 11, and an anvil roll 14. The first roll 11 and the second roll 12 are disposed so as to have their surfaces engage with each other. The anvil roll 14 is positioned so as to have its peripheral surface come into contact with the top of the projections of the first roll 11.

As illustrated in FIG. 2, an upper layer 2 and a lower layer 3 are fed from stock rolls 2' and 3', respectively. The upper layer 2 is passed through the mesh of the first and second rolls and thus embossed.

Figure 3:
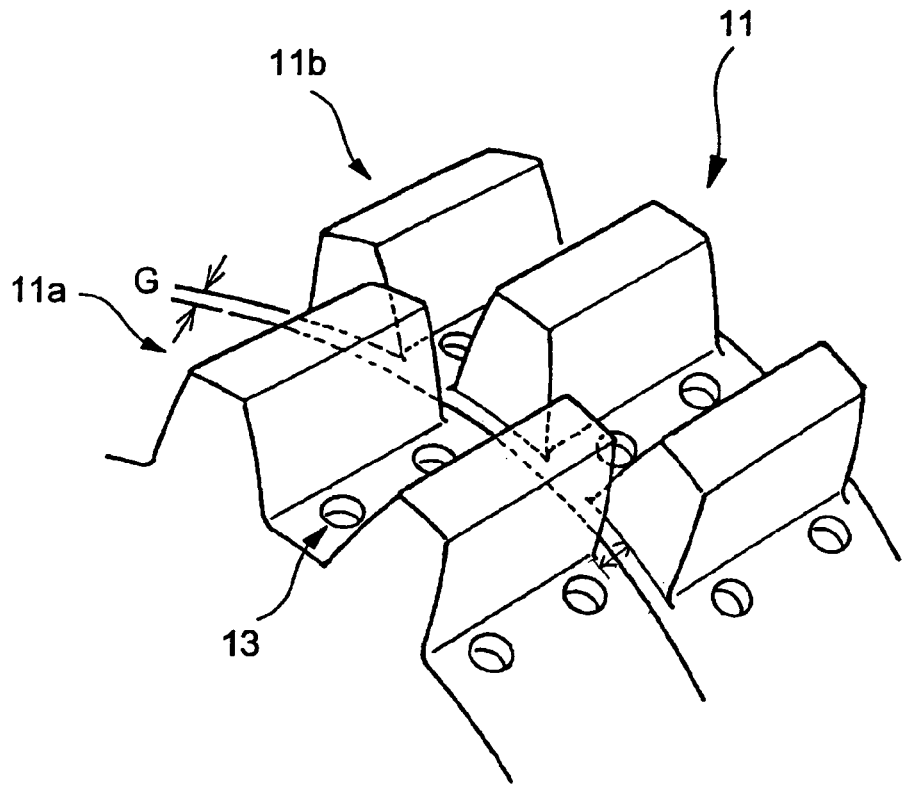
FIG. 3 is an enlarged partial view of the first roll in FIG. 2.

An enlarged view of part of the first roll 11 is shown in FIG. 3. The first roll 11 is made up of a plurality of spur gears 11a, 11b, . . . having a given face width. The face width of each gear decides the dimension of the projections 5 in Y direction. The gears are assembled into a roll form so that their teeth are out of alignment in the axial direction by half the circular pitch. As a result, the first roll 11 has discrete projections and depressions on its peripheral surface in both the axial and the rotational directions.

A suction hole 13 is bored in every bottom land of each gear of the first roll 11. The bottom land is the bottom of the depression on the surface of the first roll 11. The suction holes 13 are led to a suction source (not shown), such as a blower or a vacuum pump, and the suction paths are controlled so that the upper layer 2 is sucked while traveling from the mesh of the first and second rolls up to the meeting of the upper and lower layers. The upper layer 2 having been embossed between the first and the second rolls in mesh is tightly held to the surface of the first roll by the suction force exerted through the suction holes 13 and thus kept in the embossed shape. Adjacent gears are mounted with a prescribed gap width G therebetween as shown in FIG. 3 so that the upper layer 2 can be brought into intimate contact with the surface of the first roll 11 without imposing excessive stretching force or a cutting effect of the engagement of the two rolls to the upper layer 2. The gap G is suitably about 0.1 to 50 mm, particularly about 0.1 to 5 mm, which depends on the whole depth of the gear and the basis weight of the upper layer 2, for carrying out vacuum holding without breaking or damaging the upper layer 2. If the upper layer is not sucked, it will lift from the peripheral surface of the first roll 11, resulting in a failure to obtain a composite sheet with a desired embossed pattern.

Subsequently, as shown in FIG. 2, the upper layer 2, while being vacuum held to the first roll 11, is joined with the separately fed lower layer 3, and the laminate is introduced into the nip between the first roll 11 and the anvil roll 14. The anvil roll 14 or both the anvil roll 14 and the first roll 11 are previously heated to a prescribed temperature, whereby the lower layer 3 is thermally bonded to the upper layer 2 at the parts corresponding to the top surface of the projections on the first roll 11, i.e., the tooth faces of the gears.

The two layers may be bonded with an applied adhesive or by ultrasonic bonding instead of the thermal bonding.

The topsheet 1 shown in FIG. 1 is produced by the above-described process. Unlike the composite nonwoven fabric disclosed in JP-A-5-59655 supra, the topsheet 1 obtained by this process enjoys the advantage that projections of a given size can be formed with good reproducibility. Where in particular the first roll 11 and the second roll 12 are so configured as described above, and the gap G (see FIG. 3) of prescribed width is provided between adjacent gears, high projections 5 can be formed without breaking or damaging the upper layer 2. Thus, the resulting topsheet 1 is free from fuzz which would irritate the skin to reduce the wearing comfort.

The resulting topsheet 1 is applicable to absorbent articles such as disposable diapers, sanitary napkins, and incontinence pads. An absorbent article generally comprises a liquid permeable topsheet, a liquid impermeable backsheet, and a liquid retentive absorbent member interposed between the topsheet and the backsheet. The resulting composite sheet is also useful in other applications, such as a backsheet of an absorbent article, a base of a fastening tape used in disposable diapers with fastening tapes, a landing sheet for receiving the fastening tapes, a base of a wing used in sanitary napkins with wings, a base of a female portion of a hook & loop fastener, a cleaning sheet, and a wipe sheet.

Figure 4:
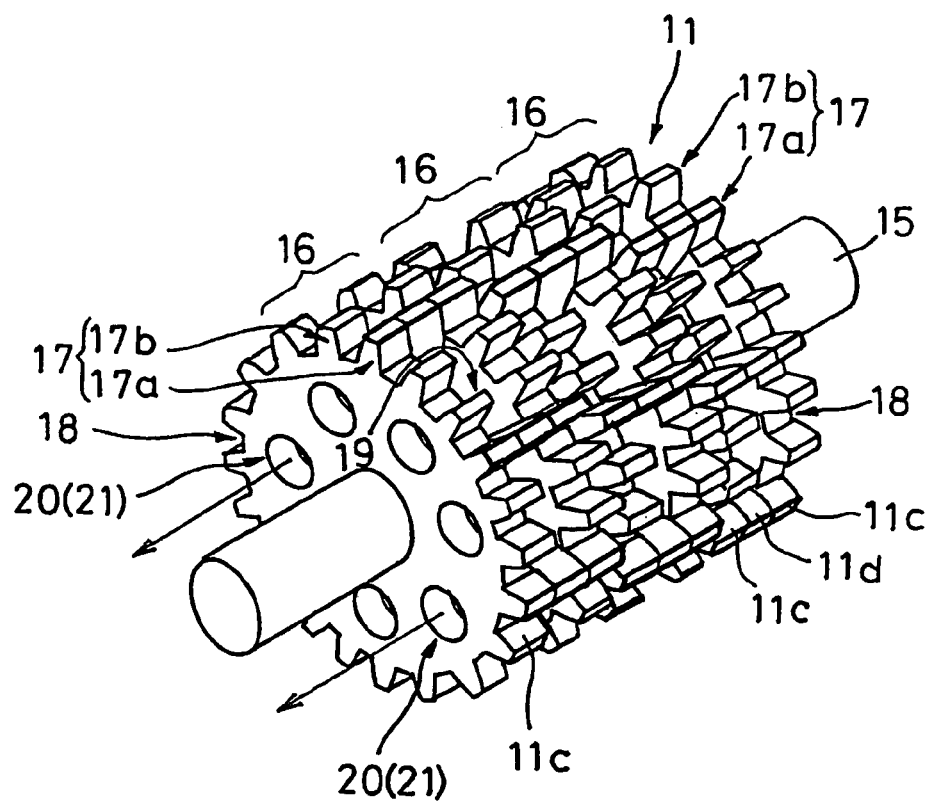
FIG. 4 is a perspective of a first roll according to another embodiment.
Figure 5:
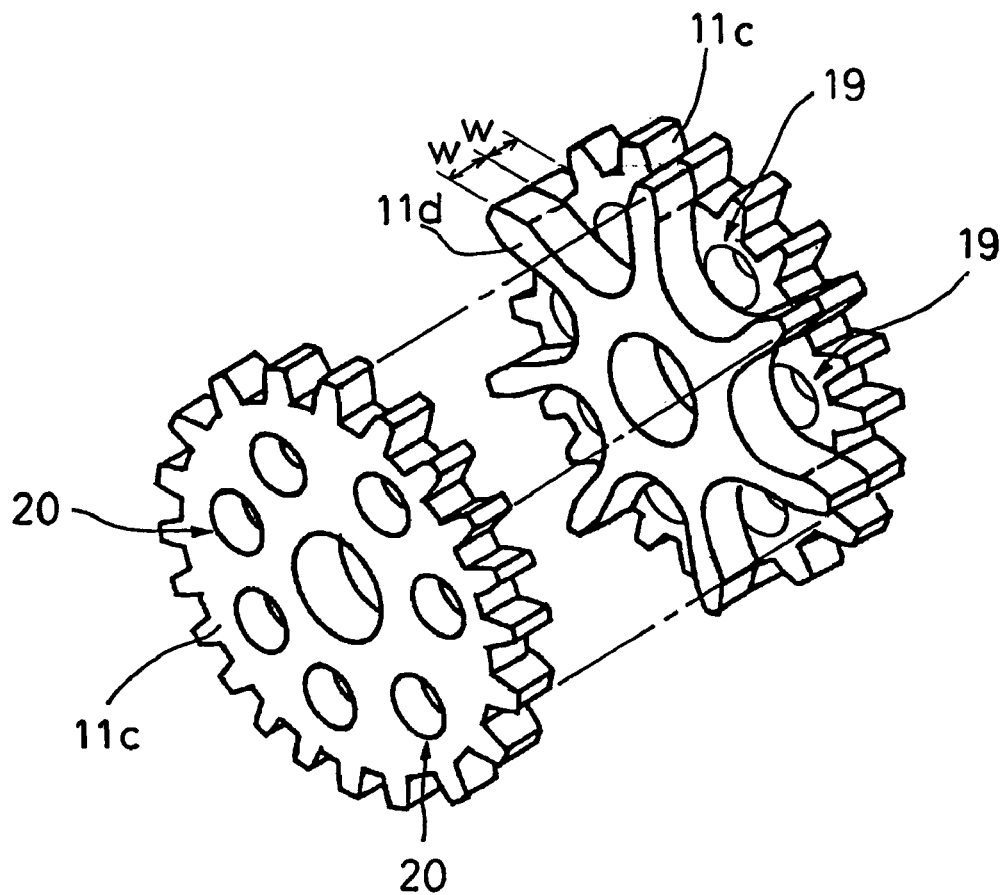
FIG. 5 is an exploded view of a part of the roll shown in FIG. 4.

FIGS. 4 and 5 show another embodiment of the first roll 11. FIG. 4 presents a perspective of the first roll 11, and FIG. 5 is an exploded view of part of the first roll 11. The roll 11 is composed of a plurality of first spur gears 11c having the same module and a plurality of second spur gears 11d having the same module, which are concentrically mounted on a rotating shaft 15. The gears 11c and 11d have the same face width. Each of the gears 11c and 11d has a through-hole in the center, through which the rotating shaft 15 is inserted. The gears 11c, the gears 11d, and the rotating shaft 15 each have a notch (not shown), and a key (not shown) is inserted into the mating notches to prevent the gears from slipping.

The first gears 11c and the second gears 11d have the same outside diameter. The number of teeth of the first gears 11c is an integer multiple of that of the second gears 11d. In the particular example shown in FIGS. 4 and 5, the number of teeth of the second gears 11d is 7, while that of the first gears 11c is 21, three times that of the second ones.

One first gear 11c is placed on both sides of one second gear 11d to make a three gear set 16. A plurality of the gear sets 16 are mounted on the shaft 15 to make the first roll 11. Two first gears 11c and one second gear 11d making each gear set 16 are combined such that their teeth are in alignment parallel to the axial direction of the roll 11. The gear set 16 has projections 17 and depressions 18 alternating in the rotating direction of the first roll 11. The projections 17 of the gear set 16 are a combination of groups of three teeth aligned in a series in the axial direction (a pair of teeth of the first gears 11c and a tooth of the second gear 11d, designated 17a in FIG. 4) and groups of two teeth discretely aligned in the axial direction (a pair of teeth of the first gears 11c, designated 17b in FIG. 4). On the other hand, the depressions 18 are spaces between adjacent teeth of each first gear 11c. The width of the projections 17 decide the dimension of the projections 5 of the topsheet 1 in Y direction.

At least two gear sets 16 are used to make the first roll 11. The gear sets 16 are mounted such that the positions of projections 17 of one gear set 16 are different from those of the adjacent gear set(s) 16 in the axial direction. In this particular example, two adjacent gear sets 16 are out of alignment by half the circular pitch of the first gear 11c.

Each gear set 16 has recesses 19 formed between a pair of the first gears 11c at a given interval along the rotational direction of the roll 11. Each recess 19 is enclosed on three sides by the pair of the first gears 11c and the intermediate second gear 11d. More specifically, each recess 19 is formed by the opposing sides of the two first gears 11c and two adjacent teeth of the second gear 11d. Accordingly, one gear set 16 has as many recesses 19 as the number of teeth of the second gear 11d. The recesses 19 are open to the outside in the above-identified depressions 18.

Each first gear 11c has through-holes 20 arranged to encircle the central through-hole through which the rotating shaft is inserted. The through-holes 20 are equal in diameter and distance from the center of the gear. They are equally spaced such that every adjacent ones make the same angle with the center of the gear. Each gear 11c has as many through-holes 20 as the number of teeth of the second gear 11d. The first gears 11c and the second gear 11d are combined to make one gear set 16 in such a configuration that each through-hole 20 may be positioned in each recess 19, i.e., between adjacent teeth of the second gear 11d. Each gear set 16 being so constructed, and a plurality of the gear sets 16 being so assembled, all the through-holes 20 connect to each other via the recesses 19 to form suction paths 21 extending in the axial direction of the first roll 11.

Figure 6:
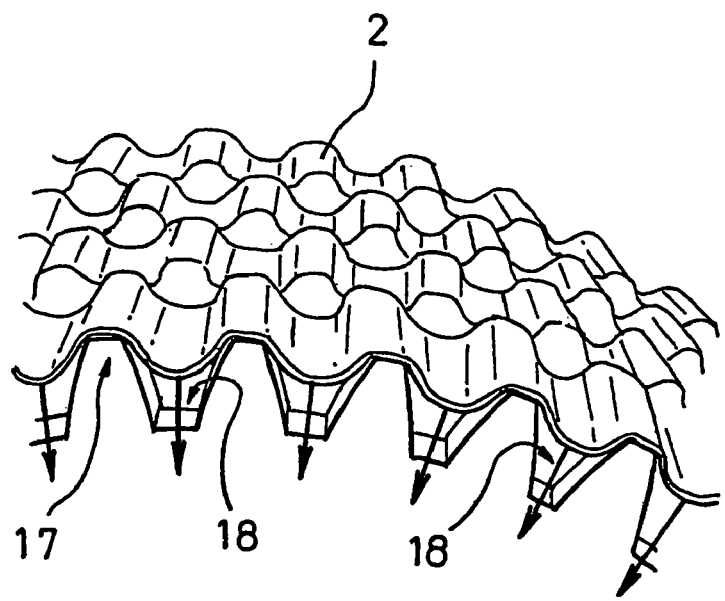
FIG. 6 shows an embossed upper layer in the state vacuum held to the first roll.

At least one end of each suction path 21 is led to a suction source (not shown) such as a blower or a vacuum pump. On operating the suction source, the roll 11 sucks air from the recesses 19 through the suction paths 21. Thus, the upper layer 2 having been embossed by the engagement of the first roll 11 and the second roll 12 is tightly held to the peripheral surface of the roll 11 and kept in the embossed shape by the suction force through the recesses 19 (see FIG. 6).

The first roll 11 according to the embodiment shown in FIGS. 4 and 5 is especially effective in producing a composite sheet with a great number of small projections at a small pitch. If the roll 11 shown in FIG. 3 is made of low module spur gears having small teeth at a small circular pitch, the suction holes 13 bored in the bottom lands cannot have but a small area. As a result, the suction force exerted on the upper layer 2 will be insufficient for tightly holding it on the surface of the first roll 11 to carry out stable embossing. In contrast, the first roll 11 according to this embodiment, even if composed of low module spur gears, can be configured to provide recesses 19 of sufficient space thereby to secure a sufficient suction path area by increasing the face width or decreasing the number of teeth of the second gears 11d. The embodiment also offers another advantage that the pitch or the size of the projections 5 can be adjusted freely by making a simple alteration to the combination of gears or the width of gears. A first roll 11 having a large number of small projections at a small pitch is effective to produce a topsheet with a soft and cushioning feel and a good appearance.

The present invention is not limited to the aforementioned embodiments. For example, with respect to the positional relationship between adjacent lines of alternating projections 5 and joints 4, the amount of positional departure from alignment in Y direction is not limited to half the pitch as with the foregoing embodiments unless the projections 5 or the joints 4 are aligned side by side to make rows in Y direction.

While in the foregoing embodiments every joint 4 is a closed depression surrounded on four sides by projections 5, it may partly adjoin other joints of adjacent lines.

While the topsheet 1 according to the foregoing embodiments is a two-ply composite sheet, the present invention includes an embodiment in which one or more additional plies contributory to specific functions are bonded to the side of the lower layer 3.

In order to improve liquid permeability of the topsheet 1, the joints, the upper layer 2 or the lower layer 3 may be perforated in parts to make holes for letting liquid through.

While in the embodiment shown in FIGS. 4 and 5 the gear sets 16 making up the first roll 11 are combined with a difference (amount of departure from alignment) of half the circular pitch in the rotational direction, the difference may be otherwise. The first gears 11*c* and the second gears 11*d* may be combined to have their teeth aligned straight in the axial direction of the first roll 11. In this case, the projections (teeth) and the depressions (spaces) form ridges and valleys extending straight over the whole width of the first roll 11 in the axial direction and alternating in the rotational direction. The composite sheet produced by using the first roll 11 thus configured has projections and depressions each extending in Y direction and alternating in X direction.

While in the embodiment shown in FIGS. 4 and 5 two first gears 11*c* and one second gear 11*d* interposed between the first gears 11*c* make one set of gears, the gear set is not limited to this combination. For example, a set of gears may be composed of at least one second gear 11*d* and at least one first gear 11*c* placed by at least one side of the second gear 11*d*.

While in the embodiment shown in FIGS. 4 and 5 recesses 19 are formed by interposing the second gear 11*d* in between a pair of the first gears 11*c*, the recesses 19 may be formed by other configurations. For example, the second gear 11*d* and the first gear 11*c* may be an integral one-piece member, which is combined with another one to form recesses 19.

While in the embodiment of FIGS. 4 and 5 all the first gears 11*c* and all the second gears 11*d* have the same face width W (see FIG. 5), the first gears and the second gears may have different face widths. Further, the face width may vary between a plurality of gear sets.

While in the embodiments of FIGS. 4 and 5 the first gears 11*c* and the second gears 11*d* have the same outside diameter, the second gears 11*d* may have a smaller outside diameter than the first gears 11*c*.

The number of teeth of the first gears 11*c* does not always need to be an integer multiple of that of the second gears 11*d* as is in the embodiment shown in FIGS. 4 and 5.

While the embossing rolls used to produce a composite sheet have been described only with reference to the first roll 11, the structure of the second roll 12 may be either the same or different from that of the first roll 11 as long as it is shaped to engage with the first roll 11. In either case, suction is not carried out in the second roll 12.

The composite sheet according to the present invention, particularly when used as a topsheet of an absorbent article, exhibits excellent leak proofness against liquid, especially a highly viscous liquid such as loose stool or menstrual blood, and high capability of hiding absorbed liquid. According to the process and the apparatus of the present invention, a composite sheet having projections of desired size at a desired pitch, especially at a small pitch, can be produced easily. It is easy with the process and the apparatus to provide a composite sheet with a vast number of tiny projections without fail. The process and the apparatus also make it feasible to reproduce projections of a given size with high accuracy. The process and the apparatus allow free variations in pitch or size of the projections by making a simple alteration to the combination of gears or the face width of gears.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A composite sheet comprising an upper layer made of a substantially inextensible sheet and a lower layer made of a substantially inextensible sheet which are partially bonded to each other at a large number of joints, the upper layer projecting outward to form a large number of hollow projections in the area other than the joints, and the projections and the joints being arranged such that the projections and the joints alternate in one direction to make lines and that the projections in each of the lines are out of alignment with the projections in the adjacent lines;

wherein the composite sheet is a sheet member of an absorbent article; and wherein each projection is a flat rectangular prism or a flat truncated quadrangular pyramid with a rectangular base and round edges.

2. The composite sheet according to claim 1, wherein each of the joints in each of the lines is surrounded on four sides by the projections.

3. The composite sheet according to claim 1, wherein the projections each have a height of 1 to 10 mm and a base area of 4 to 900 $mm^2$, and the joints each have a length of 0.1 to 20 mm in the direction of the line.

4. The composite sheet according to claim 1, which is a topsheet disposed on the wearer's side of the absorbent article with the upper layer facing a wearer, the projections projecting toward the wearer, and the lower layer facing an absorbent member side of the absorbent article.

* * * * *